United States Patent
Hoffman

(10) Patent No.: US 9,763,903 B2
(45) Date of Patent: Sep. 19, 2017

(54) COMPOSITIONS AND METHODS FOR TREATING INTESTINAL HYPERPERMEABILITY

(71) Applicant: Steven Hoffman, Mahwah, NJ (US)

(72) Inventor: Steven Hoffman, Mahwah, NJ (US)

(73) Assignee: Steven Hoffman, Mahwah, NJ (US)

( * ) Notice: Subject to any disclaimer, the term of this patent is extended or adjusted under 35 U.S.C. 154(b) by 0 days.

(21) Appl. No.: 15/059,602

(22) Filed: Mar. 3, 2016

(65) Prior Publication Data

US 2016/0193169 A1 Jul. 7, 2016

Related U.S. Application Data

(63) Continuation-in-part of application No. 14/686,545, filed on Apr. 14, 2015, now Pat. No. 9,308,188, which is a continuation of application No. 14/520,116, filed on Oct. 21, 2014, now Pat. No. 9,326,962, which is a continuation-in-part of application No. 14/062,165, filed on Oct. 24, 2013, now abandoned.

(60) Provisional application No. 61/894,261, filed on Oct. 22, 2013.

(51) Int. Cl.
| | |
|---|---|
| A61K 31/198 | (2006.01) |
| A61K 31/197 | (2006.01) |
| A61K 9/00 | (2006.01) |
| A61K 45/06 | (2006.01) |
| A61K 31/137 | (2006.01) |
| A61K 31/4166 | (2006.01) |

(52) U.S. Cl.
CPC .......... *A61K 31/198* (2013.01); *A61K 9/0053* (2013.01); *A61K 31/137* (2013.01); *A61K 31/197* (2013.01); *A61K 31/4166* (2013.01); *A61K 45/06* (2013.01)

(58) Field of Classification Search
CPC .................................................. A61K 31/198
USPC ...................................................... 514/10.7
See application file for complete search history.

(56) References Cited

U.S. PATENT DOCUMENTS

| | | |
|---|---|---|
| 4,117,161 A | 9/1978 | Pozuelo |
| 4,165,382 A | 8/1979 | Pozuelo |
| 4,189,604 A | 2/1980 | Umezawa et al. |
| 4,240,975 A | 12/1980 | Umezawa et al. |
| 5,073,541 A | 12/1991 | Taylor et al. |
| 5,206,018 A | 4/1993 | Sehgal et al. |
| 5,225,435 A | 7/1993 | Pawelek et al. |
| 5,576,290 A | 11/1996 | Hadley |
| 5,674,839 A | 10/1997 | Hruby et al. |
| 5,683,981 A | 11/1997 | Hadley et al. |
| 5,714,576 A | 2/1998 | Hruby et al. |
| 6,359,001 B1 | 3/2002 | Drago |
| 7,452,868 B2 | 11/2008 | Kuzma et al. |
| 8,003,689 B2 * | 8/2011 | Veverka ............... A61K 31/277 514/459 |
| 2002/0128304 A1 | 9/2002 | D'Amato |
| 2003/0059471 A1 | 3/2003 | Compton et al. |
| 2006/0063699 A1 | 3/2006 | Larsen |
| 2009/0030067 A1 | 1/2009 | Wosikowski-Buters |
| 2010/0216781 A1 | 8/2010 | Perrin-Ninkovic |
| 2013/0183263 A1 | 7/2013 | Hoffman |
| 2013/0243873 A1 | 9/2013 | Aversa et al. |
| 2015/0216827 A1 | 8/2015 | Hoffman |

FOREIGN PATENT DOCUMENTS

| | | |
|---|---|---|
| WO | WO 02/100885 | 12/2002 |
| WO | WO 2009/054001 | 4/2009 |
| WO | WO 2009/109649 | 9/2009 |
| WO | WO 2009/131631 | 10/2009 |
| WO | WO 2010/022243 | 2/2010 |
| WO | WO 2010/118419 | 10/2010 |
| WO | WO 2011/112576 | 9/2011 |
| WO | WO 2015-061328 A2 | 4/2015 |

OTHER PUBLICATIONS

"Standards of Medical Care in Diabetes—2013", American Diabetes Association, Jan. 2013, 36(Supp. 1), S11-S66.
Böni et al., "Radioiodine-Labelled Alpha-Methyl-Tyrosine in Malignant Melanoma: Cell Culture Studies and Results in Patients", British Journal of Dermatology, Jul. 1997, 137(1), 96-100.
Brogden, "Alpha-Methyl-P-Tyrosine: A Review of Its Pharmacology and Clinical Use", Drugs, Feb. 1981, 21(2), 81-89.
Cabrera López et al., "Effects of Rapamycin on Angiomyolipomas in Patients with Tuberous Sclerosis", Nefrologia, Apr. 2011, 31(3), 292-298.
Chen, "Progress in the Development of Bestatin Analogues as Aminopeptidases Inhibitors", Current Medical Chemistry, Mar. 2011, 18(7), 964-976.
Chhun et al., "7. The Cytochrome P-450 2C9/2C19 but not the ABCB1 Genetic Polymorphism May be Associated With the Liver Cytochrome 3A4 Induction by Phenytoin", Journal of Clinical Psychopharmacology, Jun. 2012, 32(3), 429-431.
Chiu et al., "Lipid-Based Nanoparticulate Systems for the Delivery of Anti-Cancer Drug Cocktails: Implications on Pharmacokinetics and Drug Toxicities", Current Drug Metabolism, 2009, 10, 861-874.
De Kort et al., "Leaky gut and diabetes mellitus: what is the link?", Obesity Reviews, 2011, 12, 449-458.
Dorr et al., "Evaluation of Melanotan-II, a Superpotent Cyclic Melanotropic Peptide in a Pilot Phase-I Clinical Study", Life Sciences, Apr. 1996, 58(20), 1777-1784.

(Continued)

*Primary Examiner* — Rei-Tsang Shiao
(74) *Attorney, Agent, or Firm* — Baker Hostetler LLP

(57) ABSTRACT

The present invention provides methods, compositions, and kits for treating intestinal hyperpermeability in a subject in need thereof, including conditions such as hyperglycemia and underlying diseases such as diabetes, autism, fibromyalgia, inflammatory bowel disease (IBD), graft versus host disease (GVHD), HIV/AIDS, multiple organ dysfunction syndrome, irritable bowel syndrome (IBS), celiac disease, eczema, psoriasis, acute pancreatitis, Parkinson's disease, depression, chronic fatigue syndrome, asthma, multiple sclerosis, arthritis, ankylosing spondylitis, nonalcoholic fatty liver disease, alcoholic cirrhosis, environmental enteropathy, or kwashiorkor.

28 Claims, 1 Drawing Sheet

(56) References Cited

OTHER PUBLICATIONS

Ell, "Brain Tumor Uptake of Iodo-Alpha-Methyl-Tyrosine", Journal of Nuclear Medicine, Nov. 1991, 32(11), 2193-2194.
Espeillac et al., "S6 kinase 1 is Required for Rapamycin-Sensitive Liver Proliferation After Mouse Hepatectomy", The Journal of Clinical Investigation, Jul. 2011, 121(7), 2821-2832.
Fan et al., "Impact of System L Amino Acid Transporter 1 (LAT1) on Proliferation of Human Ovarian Cancer Cells: A Possible Target for Combination Therapy with Anti-Proliferative Aminopeptidase Inhibitors", Biochemical Pharmacology, Sep. 15, 2010, 80(6), 811-818.
Fitzgerald et al., "Effect of Melanotan, [Nle(4), D-Phe(7)]-Alpha-MSH, on Melanin Synthesis in Humans with MC1R Variant Alleles", Peptides, Feb. 2006, 27(2), 388-394.
Ichimura et al., "Immunohistochemical Expression of Aminopeptidase N (CD13) in Human Lung Squamous Cell Carcinomas, with Special Reference to Bestatin Adjuvant Therapy", Pathology International, Jun. 2006, 56(6), 296-300.
Kargiotis et al., "Epilepsy in the Cancer Patient", Cancer Chemotherapy and Pharmacology, Mar. 2011, 67(3), 489-501.
Krige et al., "CHR-2797: An Antiproliferative Aminopeptidase Inhibitor that Leads to Amino Acid Deprivation in Human Leukemic Cells", Cancer Research, Aug. 15, 2008, 68(16), 6669-6679.
Kulke et al., "Future Directions in the Treatment of Neuroendocrine Tumors: Consensus Report of the National Cancer Institute Neuroendocrine Tumor Clinical Trials Planning Meeting", Journal of Clinical Oncology, Mar. 2011, 29(7), 934-943.
Landmark, "Antiepileptic Drugs in Non-Epilepsy Disorders—Relations between Mechanisms of Action and Clinical Efficacy", CNS Drugs, 2008, 22(1), 27-47.
Liu et al., "Combinatorial Effects of Lapatinib and Rapamycin in Triple-Negative Breast Cancer Cells", Molecular Cancer Therapeutics, Aug. 2011, 10, 1460-1469.
Longo et al., "Efficacy and Tolerability of Long-Acting Octreotide in the Treatment of Thymic Tumors: Results of a Pilot Trial", American Journal of Clinical Oncology, Apr. 2012, 35(2), 105-109.
Nakagami, "A Case of Malignant Pheochromocytoma Treated with 131i-Metaiodobenzylguanidine and Alpha-Methyl-P-Tyrosine", Japanese Journal of Medicine, May-Jun. 1990, 29(3), 329-333.
Ram et al., "Failure of Alpha-Methyltyrosine to Prevent Hypertensive Crisis in Pheochromocytoma", Archives of Internal Medicine, Nov. 1985, 145(11), 2114-2115.
Ryakhovsky et al., "The First Preparative Solution Phase Synthesis of Melanotan II", Beilstein Journal of Organic Chemistry, 2008, 4, 1-6.
Steinsapir et al., "Metyrosine and Pheochromocytoma", Archives of Internal Medicine, Apr. 1997, 157(8), 901-906.
Tada, "Three cases of Malignant Pheochromocytoma Treated with Cyclophosphamide, Vincristine, and Dacarbazine Combination Chemotherapy and Alpha-Methyl-P-Tyrosine to Control Hypercatecholaminemia", Hormone Research, Jan. 1998, 49(6), 295-297.
Taveria-DaSilva, "Sirolimus Therapy in Patients with Lymphangioleiomyomatosis", Summaries for patients, Annals of Internal Medicine, Jun. 21, 2011, 154(12), I44.
Terauchi et al., "Inhibition of APN/CD 13 Leads to Suppressed Progressive Potential in Ovarian Carcinoma Cells", BMC Cancer, 2007, 7, 1-12.
Tsukamoto et al., "Aminopeptidase N (APN)/CD13 Inhibitor, Ubenimex, Enhances Radiation Sensitivity in Human Cervical Cancer", BMC Cancer, Mar. 2008, 8(74), 8 pages.
Voorhess, "Effect of Alpha-Methyl-P-Tyrosine on 3,4-Dihydroxyphenylalanine (DOPA) Excretion of Hamsters with Melanotic Melanoma", Cancer Research, Mar. 1968, 28, 452-454.
Zimmermann et al., "Prolonged Inhibition of Presynaptic Catecholamine Synthesis With α-Methyl-Para-Tyrosine Attenuates the Circadian Rhythm of Human TSH Secretion" J. Soc. Gynecol Investing, May/Jun. 2001, 8(3), 174-178.
Russo, A.J., "Correlation Between Hepatocyte Growth Factor (HGF) and Gamma-Aminobutyric Acid Plasma (GABA) Plasma Levels in Autistic Children", Biomarker Insights, 2013, 8, 69-75.

* cited by examiner

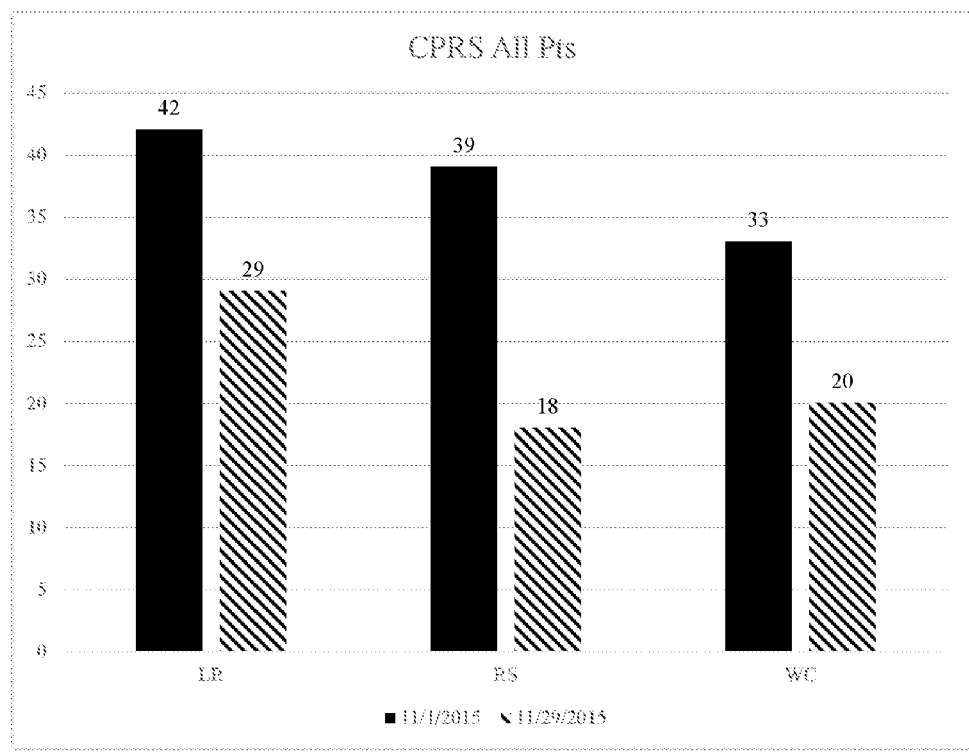

COMPOSITIONS AND METHODS FOR TREATING INTESTINAL HYPERPERMEABILITY

CROSS-REFERENCE TO RELATED APPLICATIONS

This application is a continuation-in-part of U.S. application Ser. No. 14/686,545, filed Apr. 14, 2015, which is a continuation of U.S. patent application Ser. No. 14/520,116, filed Oct. 21, 2014, which is a continuation-in-part of U.S. patent application Ser. No. 14/062,165, filed Oct. 24, 2013, which claims the benefit of U.S. Provisional Patent Application No. 61/894,261, filed Oct. 22, 2013, the entireties of which are incorporated by reference herein.

TECHNICAL FIELD

The present inventions relate generally to compositions, kits, and methods for the treatment of intestinal hyperpermeability.

BACKGROUND

The intestinal epithelium separates luminal contents from the interstitium. This function is primarily determined by the integrity of the epithelium and the tight junction that seals the paracellular space. These intestinal tight junctions are selectively permeable. This permeability can be increased physiologically in response to the presence of luminal nutrients. Permeability can also be increased pathologically by mucosal immune cells and cytokines, the enteric nervous system, and by pathogens. It is believed to be critical that the intestinal mucosa prevent potentially dangerous contents of the intestinal lumen, including the microorganisms that reside there from entering internal areas and the systemic circulation. There are several clinical conditions, both intestinal and systemic, that are associated with compromised intestinal barrier function.

A possible link between intestinal hyperpermeability and disease has been proposed. This has led to a sharp increase in the diagnosis of intestinal hyperpermeability, also known as "leaky gut syndrome." Diseases that have been correlated with intestinal hyperpermeability include diabetes, autism, fibromyalgia, inflammatory bowel disease (IBD), graft versus host disease (GVHD), HIV/AIDS, multiple organ dysfunction syndrome, irritable bowel syndrome (IBS), celiac disease, eczema, psoriasis, acute pancreatitis, Parkinson's disease, depression, chronic fatigue syndrome, asthma, multiple sclerosis, arthritis, ankylosing spondylitis, nonalcoholic fatty liver disease, alcoholic cirrhosis, environmental enteropathy, and kwashiorkor. It is believed that restoration of the intestinal barrier will improve or cure the underlying disease. Several drug targets that could potentially promote barrier restoration have been proposed, but none have proven safe and effective.

Thus, there remains a need for the development of safe and effective treatments or cures for intestinal hypersensitivity and numerous underlying diseases.

SUMMARY

The present invention provides methods, compositions, and kits for treating intestinal hyperpermeability in a subject in need thereof, including underlying conditions including hyperglycemia, and including underlying diseases such as diabetes, autism, fibromyalgia, inflammatory bowel disease (IBD), graft versus host disease (GVHD), HIV/AIDS, multiple organ dysfunction syndrome, irritable bowel syndrome (IBS), celiac disease, eczema, psoriasis, acute pancreatitis, Parkinson's disease, depression, chronic fatigue syndrome, asthma, multiple sclerosis, arthritis, ankylosing spondylitis, nonalcoholic fatty liver disease, alcoholic cirrhosis, environmental enteropathy, or kwashiorkor. In certain embodiments, the invention provides methods comprising administering to a subject in need thereof an effective amount of a tyrosine hydroxylase inhibitor. In certain embodiments, the invention provides methods comprising administering to a subject in need thereof an effective amount of a tyrosine hydroxylase inhibitor and a p450 3A4 promoter.

In other embodiments, the invention provides pharmaceutical compositions comprising a tyrosine hydroxylase inhibitor and a p450 3A4 promoter. Also provided are kits comprising a tyrosine hydroxylase inhibitor and a p450 3A4 promoter together with packaging for same.

BRIEF DESCRIPTION OF THE DRAWINGS

FIG. 1 depicts Conners Parent Rating Scale Data results.

DETAILED DESCRIPTION OF ILLUSTRATIVE EMBODIMENTS

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder. This condition, disease or disorder can be intestinal hyperpermeability.

With respect to autism, for example, the adverse or negative effect or symptoms can include any of those that are the subject of the diagnostic criteria specified for autism spectrum disorder in the American Psychiatric Association's Diagnostic and Statistical Manual, Fifth Edition (DSM-5, DSM-V), the contents of which are incorporated by reference herein, e.g., deficits in social-emotional reciprocity (ranging, for example, from abnormal social approach and failure of normal back-and-forth conversation; to reduced sharing of interests, emotions, or affect; to failure to initiate or respond to social interactions) deficits in nonverbal communicative behaviors used for social interaction (ranging, for example, from poorly integrated verbal and nonverbal communication; to abnormalities in eye contact and body language or deficits in understanding and use of gestures; to a total lack of facial expressions and nonverbal communication); deficits in developing, maintaining, and understanding relationships (ranging, for example, from difficulties adjusting behavior to suit various social contexts; to difficulties in sharing imaginative play or in making friends; to absence of interest in peers); stereotyped or repetitive motor movements, use of objects, or speech (e.g., simple motor stereotypes, lining up toys or flipping objects, echolalia, idiosyncratic phrases); insistence on sameness, inflexible adherence to routines, or ritualized patterns of verbal or nonverbal behavior (e.g., extreme distress at small changes, difficulties with transitions, rigid thinking patterns, greeting rituals, need to take same route or eat same food every day); highly restricted, fixated interests that are abnormal in intensity or focus (e.g., strong attachment to or preoccupation with unusual objects, excessively circumscribed or perseverative interests); and hyper- or hyporeactivity to sensory input or unusual interest in sensory aspects of the environment (e.g. apparent indifference to pain/temperature, adverse response to specific sounds or textures, excessive smelling or touching of objects, visual fascination with lights or movement).

Some subpopulations of patients on the autism spectrum, including those patients diagnosed with Asperger's Disorder (i.e., Asperger Syndrome) or Social Communication Disorder, exhibit symptoms of Attention Deficit Hyperactivity Disorder (ADHD) (e.g., inattention, hyperactivity, and impulsivity) and/or tics (motor tics or vocal tics). See, e.g., DSM-5.

Assessment of autism symptoms, or any of the symptoms of the present disclosure, can be performed using methods known in the art. For example, one method of assessing autism symptoms is the Clinical Global Impressions (CGI) scale based upon changes from baseline in various psychometric tests. These tests can include the Aberrant Behavior Checklist-Community (ABC-C), Conners Parent Rating Scale and the Autism Diagnostic Observation Schedule (ADOS). Autism symptoms can also be assessed from the clinician's personal, clinical observations, from videographic information taken at regularly scheduled clinic visits, and from information provided by the subject's caregivers over time. Compositions and methods of the disclosure result in a reduction of at least 1 point in at least one dimension of the Conners Parent Rating Scale assessment score.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with respect to the particular compound, component or composition selected, the route of administration, and the ability of the components to elicit a desired result in the individual, but also with respect to factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide improved therapeutic response. An effective amount is also one in which any toxic or detrimental effects of the components are outweighed by the therapeutically beneficial effects.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"High blood glucose level" is used interchangeably with "hyperglycemia" herein and is defined as a fasting plasma blood glucose level of 126 mg/dl or greater on two separate occasions, Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein can be prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein that contain, for example, both amino and carboxy groups, also include reference to their corresponding zwitterions.

The term "stereoisomers" refers to compounds that have identical chemical constitution, but differ as regards the arrangement of the atoms or groups in space. The term "enantiomers" refers to stereoisomers that are mirror images of each other that are non-superimposable.

The term "administering" means either directly administering a compound or composition of the present invention, or administering a prodrug, derivative or analog which will form an equivalent amount of the active compound or substance within the body.

The terms "subject," "individual," and "patient" are used interchangeably herein, and refer to an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

The term "inhibitor" as used herein includes compounds that inhibit the expression or activity of a protein, polypeptide or enzyme and does not necessarily mean complete inhibition of expression and/or activity. Rather, the inhibition includes inhibition of the expression and/or activity of a protein, polypeptide or enzyme to an extent, and for a time, sufficient to produce the desired effect.

The term "promoter" as used herein includes compounds that promote the expression or activity of a protein, polypeptide or enzyme and does not necessarily mean complete promotion of expression and/or activity. Rather, the promotion includes promotion of the expression and/or activity of a protein, polypeptide or enzyme to an extent, and for a time, sufficient to produce the desired effect.

While not intending to be bound by any particular mechanism of operation, it is believed that the tyrosine hydroxylase inhibitors according to the present invention function by decreasing the amount of adrenaline secreted into the bloodstream.

Methods of treating intestinal hyperpermeability in a subject are provided. Such methods can include administering to a subject in need thereof an effective amount of a tyrosine hydroxylase inhibitor. Other such methods include administering to a subject in need thereof an effective amount of tyrosine hydroxylase inhibitor and a p450 3A4 promoter. This tyrosine hydroxylase inhibitor and the p450 3A4 promoter can be administered simultaneously.

Administration of the tyrosine hydroxylase inhibitor or the tyrosine hydroxylase inhibitor and the p450 3A4 promoter can be through various routes, including orally, nasally subcutaneously, intravenously, intramuscularly, transdermally, vaginally, rectally or in any combination thereof. Transdermal administration can be effected using, for example, oleic acid, 1-methyl-2-pyrrolidone, dodecylnonaoxyethylene glycol monoether.

In other suitable embodiments of the invention the tyrosine hydroxylase inhibitor and the p450 3A4 promoter are administered during a cycle consisting of five to seven days of administering the tyrosine hydroxylase inhibitor and the p450 3A4 promoter, and one to two days of not administering the tyrosine hydroxylase inhibitor and the p450 3A4 promoter. In some suitable embodiments of the invention, at least six of said cycles of administration are performed. In some suitable embodiments of the invention, 25 mg of the tyrosine hydroxylase inhibitor is administered.

In certain embodiments, the tyrosine hydroxylase inhibitor is a tyrosine derivative. The tyrosine derivative can be capable of existing in different isomeric forms, including stereoisomers and enantiomers. The tyrosine derivative can, for example, exist in both L-form or D-form. The tyrosine derivative can, for example, also exist in a racemic form. Representative tyrosine derivatives include one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy]phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl)oxy]benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine methyl ester hydrochloride, H-3,5-diiodo-tyrosine methyl ester hydrochloride, H-D-3,5-diiodo-tyrosine methyl ester hydrochloride, H-D-tyrosine methyl ester hydrochloride, D-tyrosine methyl ester hydrochloride, D-tyrosine-methyl ester hydrochloride, methyl D-tyrosinate hydrochloride, H-D-tyrosine methyl ester.hydrochloride, D-tyrosine methyl ester hydrochloride, H-D-tyrosine methyl ester-hydrochloride, (2R)-2-amino-3-(4-hydroxyphenyl) propionic acid, (2R)-2-amino-3-(4-hydroxyphenyl)methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5-I2)-OSu, Fmoc-tyrosine(3-NO2)-OH, α-methyl-L-tyrosine, α-methyl-D-tyrosine, and α-methyl-DL-tyrosine. In certain embodiments of the invention, the tyrosine derivative is α-methyl-L-tyrosine. In other embodiments, the tyrosine derivative is α-methyl-D-tyrosine. In other embodiments, the tyrosine derivative is α-methyl-DL-tyrosine in a racemic form.

In methods of the invention, 60 mg of the tyrosine derivative is administered orally and 0.25 mL of a 2 mg/mL suspension of the tyrosine derivative is administered subcutaneously.

Representative p450 3A4 promoters include 5,5-diphenylhydantoin, valproic acid and carbamazepine. In a suitable embodiment of the invention, the composition includes 5 mg to 25 mg of 5,5-diphenylhydantoin. Representative subjects include mammals. In certain embodiments, the mammal is a human.

In some embodiments of the invention, methods further comprising assessing progression of said intestinal hyperpermeability in said subject are provided. This assessing step can be performed before said administering step or after said administering step.

Representative conditions that can be treated with methods of the present invention include hyperglycemia. Symptoms of the condition hyperglycemia can include: polyphagia, polydipsia, polyuria, blurred vision, fatigue (sleepiness), weight loss, poor wound healing (cuts, scrapes, etc.), dry mouth, dry or itchy skin, tingling in feet or heels, erectile dysfunction, recurrent infections, external ear infections (swimmer's ear), cardiac arrhythmia, stupor, coma, and seizures. Representative diseases that can be treated with methods of the present invention include diabetes, autism, fibromyalgia, inflammatory bowel disease (IBD), graft versus host disease (GVHD), HIV/AIDS, multiple organ dysfunction syndrome, irritable bowel syndrome (IBS), celiac disease, eczema, psoriasis, acute pancreatitis, Parkinson's disease, depression, chronic fatigue syndrome, asthma, multiple sclerosis, arthritis, ankylosing spondylitis, nonalcoholic fatty liver disease, alcoholic cirrhosis, environmental enteropathy, or kwashiorkor.

Administration of pharmaceutically active molecules such as inhibitor and/or promoters can be through various routes, including orally, nasally, subcutaneously, intravenously, intramuscularly, transdermally, vaginally, rectally or in any combination thereof. Transdermal administration can be effected using, for example, oleic acid, 1-methyl-2-pyrrolidone, dodecylnonaoxyethylene glycol monoether.

The tyrosine hydroxylase inhibitor can be administered during a cycle consisting of five to seven days of administering the tyrosine hydroxylase inhibitor, and one to two days of not administering the tyrosine hydroxylase inhibitor. The tyrosine hydroxylase inhibitor can be administered over the course of at least six said cycles. In one suitable embodiment of the invention, the tyrosine hydroxylase inhibitor is administered daily. In another suitable embodiment of the invention, the tyrosine hydroxylase inhibitor is administered multiple times per day.

Representative treatment methods according to the invention comprise administering to a subject in need thereof an effective amount of a tyrosine hydroxylase inhibitor or a tyrosine hydroxylase inhibitor and a p450 3A4 promoter are provided.

Suitable embodiments can include a pharmaceutical composition comprising a tyrosine hydroxylase inhibitor and a p450 3A4 promoter. The tyrosine hydroxylase inhibitor can be a tyrosine derivative.

Preferred aspects of the disclosure are directed to methods of treating autism in a patient by administering an effective amount of α-methyl-DL-tyrosine to the patient. These methods result in the reduction of at least one of the diagnostic markers of autism, as defined in the DSM-5. These methods also result in a reduction of at least one of the dimensions assessed using the Aberrant Behavior Checklist-Community (ABC-C), Autism Diagnostic Observation Schedule (ADOS), and/or Conners Parent Rating Scale (CPRS). According to these aspects, about 10-2000 mg of the α-methyl-DL-tyrosine is administered daily, preferably, 150-300 mg of the α-methyl-DL-tyrosine is administered daily. The α-methyl-DL-tyrosine is preferably administered orally. The daily dosages can be administered as a single dose or in substantially equal doses throughout the day. Three, substantially equal daily doses of the α-methyl-DL-tyrosine are particularly preferred.

In some of these aspects, γ-aminobutyric acid (GABA) can be administered with the α-methyl-DL-tyrosine. The GABA can be administered simultaneously with the α-methyl-DL-tyrosine. In other aspects, the GABA can be administered separately from the α-methyl-DL-tyrosine, i.e., at another time during the day. In some aspects, the GABA is administered at bedtime. Typically dosages of the GABA are from about 5 mg to about 30 mg, for example, 5, 10, 15, 20, 25, or about 30 mg of GABA., with 15 mg of GABA being particularly preferred.

In other of these aspects, a p450 3A4 promoter is administered in addition to the α-methyl-DL-tyrosine and the optional GABA. Preferred p450 3A4 promoters include 5,5-diphenylhydantoin, valproic acid, and carbamazepine.

Those subjects on the autism spectrum, including those diagnosed with Asperger's Disorder (Asperger Syndrome) or Social Communication Disorder, who also have symptoms of ADHD and/or tics can be treated using methods of the disclosure. In these aspects, the subject can be administered an effective amount of a tyrosine hydroxylase inhibitor and an effective amount of a beta adrenergic agonist (also referred to as beta agonists). The tyrosine hydroxylase inhibitor can be any of the tyrosine hydroxylase inhibitors described herein, with α-methyl-DL-tyrosine being particularly preferred. Beta adrenergic agonists are known in the art and include, for example, albuterol, levalbuterol, fenoterol, formoterol, isoproterenol, metaproterenol, salmeterol, terbutaline, clenbuterol, isoetarine, pirbuterol, procaterol, ritodrine, epinephrine, and combinations thereof. Albuterol is a particularly preferred beta adrenergic agonist.

In certain of these aspects, the tyrosine hydroxylase inhibitor and the beta adrenergic inhibitor are administered simultaneously. In other aspects, the beta adrenergic inhibitor is administered separately from the -methyl-DL-tyrosine, i.e., at another time during the day. According to these aspects, about 10-2000 mg of the tyrosine hydroxylase inhibitor (e.g., α-methyl-DL-tyrosine) is administered daily, preferably, 150-300 mg of the tyrosine hydroxylase inhibitor (e.g., α-methyl-DL-tyrosine) is administered daily. The tyrosine hydroxylase inhibitor (e.g., α-methyl-DL-tyrosine) is preferably administered orally. The daily dosages can be administered as a single dose or in substantially equal doses throughout the day. Three, substantially equal daily doses of the tyrosine hydroxylase inhibitor (e.g., α-methyl-DL-tyrosine) are particularly preferred.

According to the disclosure, the described methods for treating a disease or disorder can be used in combination with treatment methods that are also known to be effective in treating the same disease or disorder. For example, autism behaviors and symptoms can be treated with compounds that affect autonomic neurotransmission (e.g. amphetamine, methylphenidate, and the like), psychotopic drugs (e.g., risperidone), neutotransmitter reuptake inhibitors (e.g., fluoxetine), compounds that stimulate glutaminergic transmission (e.g., LY2140023), and/or compounds that affect cholinergic neurotransmission (e.g., galantamine). As such, the disclosure is also directed to methods of treating autism in a patient by administering an effective amount of α-methyl-DL-tyrosine and an effective amount of a compound that affects autonomic neurotransmission, a psychotopic drug, a neutotransmitter reuptake inhibitor, a compound that stimulates glutaminergic transmission, and/or a compound that affects cholinergic neurotransmission.

Also provided herein are kits comprising a tyrosine hydroxylase inhibitor and a p450 3A4 promoter together with packaging for same. The tyrosine hydroxylase inhibitor can be a tyrosine derivative. The tyrosine derivative can include tyrosine derivatives capable of existing in isomeric form. The tyrosine derivatives can include tyrosine derivatives in its L-form or in its D-form. The tyrosine derivative can, for example, also exist in a racemic form. Representative tyrosine derivatives include one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy]phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl)oxy]benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine-methyl ester hydrochloride, H-3,5-diiodo-tyrosine-methyl ester hydrochloride, H-D-3,5-diiodo-tyrosine-methyl ester hydrochloride, H-D-tyrosine-methyl ester hydrochloride, D-tyrosine methyl ester hydrochloride, D-tyrosine-ome hydrochloride, methyl D-tyrosinate hydrochloride, H-D-tyrosine-methyl ester.hydrochloride, D-tyrosine methyl ester hydrochloride, H-D-tyrosine-methyl ester-hydrochloride, (2R)-2-amino-3-(4-hydroxyphenyl) propionic acid, (2R)-2-amino-3-(4-hydroxyphenyl)methyl ester hydrochloride, methyl (2R)-2-amino-3-(4-hydroxyphenyl) propanoate hydrochloride methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5-I2)-OSu, Fmoc-tyrosine(3-NO2)-OH, α-methyl-L-tyrosine, α-methyl-D-tyrosine, and α-methyl-DL-tyrosine. In certain embodiments of the invention, the tyrosine derivative is α-methyl-L-tyrosine. In other specific embodiments of the invention, the tyrosine derivative is α-methyl-D-tyrosine. In other embodiments, the tyrosine derivative is α-methyl-DL-tyrosine in a racemic form.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1

Two-hundred patients were initially screened. Thirty subjects meeting the study criteria consented. Nine (9) subjects had high blood glucose levels (hyperglycemia) prior to consenting to the study.

A high blood glucose level (hyperglycemia) is defined as a fasting plasma blood glucose level of 126 mg/dl or greater on two separate occasions, The average patient age was sixty-two years old and the median patient age was sixty years old. Six of the patients were female and three of the patients were male. Five of the patients were fifty to sixty years old and four of the patients were over the age of sixty.

The patients in the study were administered a treatment regimen that included a tyrosine hydroxylase inhibitor (i.e., α-methyl-DL tyrosine), a melanin promoter (i.e., melanotan II), a p450 3A4 promoter (i.e., 5,5-diphenylhydantoin), and a leucine aminopeptidase inhibitor (i.e., N-[(2S,3R)-3-amino-2-hydroxy-4-phenylbutyryl]-L-leucine). These compounds were administered on each of five days per week for a period of six weeks, with one or two days off between weekly cycles. Blood glucose level was monitored for all subjects biweekly. Blood glucose levels were determined by daily blood glucose tests followed-up with laboratory blood glucose tests every two weeks.

After approximately two to four weeks, all nine of the subjects had normal blood glucose levels defined as a fasting plasma blood glucose level of 125 mg/dl or lower on two separate occasions.

Overall, the above-noted treatment was well tolerated by the subjects, with no adverse events related to the treatment, and responses have been documented to the treatment 100%.

Example 2

Patients are screened and the extent to which they meet the DSM-V criteria for autism spectrum disorder is assessed. A subgroup of those satisfying the criteria are administered a treatment regimen that includes a tyrosine hydroxylase inhibitor (i.e., α-methyl-DL tyrosine) at dose of 50-100 mg three times daily. Another subgroup is administered a treatment regimen that further includes a p450 3A4 promoter (i.e., 5,5-diphenylhydantoin) in one daily dose of 30 mg. Gamma-aminobutyric acid is optionally administered to both subgroups at bedtime at a dose of 15 mg to aid sleeping and to quiet ticks and repetitive behaviors like teeth grinding. Vasopressin is administered as needed to assist brain governance. Following each administration of the treatment regimen, changes in the extent to which the subjects satisfy the DSM-5 criteria is again assessed.

Example 3

A Blinded, Randomized, Placebo Controlled Phase 2 Study for the Use of AMPT in the Treatment of Autism Study Design: Blinded, randomized, 2 arm, 8-week treatment period followed by additional follow-up visits off treatment over the next 18 weeks for a total of 26 weeks' study participation. Treatment arms consist of L1-79 alone or placebo.

Sample Size:L1-79 N=30, placebo N=10

Study Population: Autistic patients over 12 years of age that meet the entry criteria and who are high performing in the opinion of the investigator.

Major Inclusion Criteria: Signed informed consent, normal clinical laboratory values, DSM-5 compliant diagnosis of autism, Qualifying ADOS score, sufficiently high functioning to complete the protocol, no psychotropic drugs for at least 2 weeks, ABC-C score >12.

Major Exclusion Criteria: Fragile-X syndrome, epilepsy, use of complimentary alternative medications, any co-morbidities, other psychiatric disorder, out of range lab values.

Experimental Treatment: L1-79 is a racemic form of the drug Demser. It will be given daily×8 weeks, and then followed on weeks 10, 13 and 26.

Non-Experimental Treatment: Placebo.

Dosage and Administration: L1-79 or placebo, as randomized, will be administered orally at a dose of 90 mg TID.

Evaluation Schedule: Patients will receive 8 weeks of the schedule above with weekly treatment evaluations for weeks 1-8 then post-treatment follow up visits at weeks 10, 13 & 26.

Safety Measures: Regularly scheduled complete history and physical examination, vital signs, CBC, differential, platelet counts, urine analysis, serum enzymes including: total protein, albumin, glucose, BUN, creatinine, direct and total bilirubin, alkaline phosphatase, phosphorous, calcium, AST, ALT, sodium, potassium, chloride, bicarbonate, $T_4$, TSH, and adverse events assessments. An independent DMC will oversee the conduct of this trial to assure patient safety.

Study Duration: A maximum of 50 weeks (12 weeks' enrollment, 38 weeks' treatment and follow-up).

Study Endpoints: The primary end point will be the assessment of the attending physician as reflected in the Clinical Global Impressions (CGI) scale based upon changes from baseline in various psychometric tests, including the Aberrant Behavior Checklist-Community (ABC-C), Conners Parent Rating Scale and the Autism Diagnostic Observation Schedule (ADOS), as well as from their personal observations in the clinic, and from videographic information taken at regularly scheduled clinic visits (per this protocol) and provided by caregivers over the course of this study.

Example 4

α-methyl-DL tyrosine (AMPT) was administered to 3 patients. This group of patients was qualified under the DSM-5 definition of autism and treated. See Table 1

TABLE 1

| Patient number | Age | Sex | Dosage AMPT | Adverse Events |
|---|---|---|---|---|
| 01-001 | 3 | Male | 90 TID | None |
| 01-002 | 15 | Male | 90 TID | None |
| 01-003 | 11 | Male | 90 TID | None |

The Aberrant Behavior Checklist-Community (ABC-C), Autism Diagnostic Observation Schedule (ADOS), Conners Parent Rating Scale (CPRS), and General Clinical Impressions scale were used to assess the disease. Videos were taken at each visit.

Data for two of these patients over the first 3 weeks of this observation are presented in the tables below. Conners Patent Rating Scale Data is depicted in FIG. 1. These clinical improvements appear to begin quickly and are durable. Continued improvement over weeks and months has been observed. No adverse events have been reported other than mild tiredness on the first day of dosing in two patients.

TABLE 2

| PT LR | | \multicolumn{5}{c}{Date of Assessment} | | | | |
|---|---|---|---|---|---|---|
| Test | Dimension | initial | Day 7 | Day 14 | Day 21 | Day 28 |
| ABC-C | TOTAL | 114 | 71 | 55 | 53 | 53 |
|  | irritability | 21 | 16 | 16 | 16 | 16 |
|  | lethargy | 31 | 12 | 8 | 7 | 7 |
|  | stereotypy | 13 | 5 | 0 | 0 | 0 |
|  | hyperactivity | 34 | 31 | 24 | 23 | 23 |
|  | speech | 5 | 7 | 7 | 7 | 7 |

TABLE 2-continued

| PT LR | | Date of Assessment | | | | |
|---|---|---|---|---|---|---|
| Test | Dimension | initial | Day 7 | Day 14 | Day 21 | Day 28 |
| DSM-V | TOTAL | 42 | 27 | 21 | 18 | 18 |
|  | social | 9 | 5 | 3 | 2 | 2 |
|  | communication | 10 | 4 | 3 | 2 | 2 |
|  | relationships | 11 | 4 | 3 | 2 | 2 |
|  | behavior | 12 | 12 | 12 | 12 | 12 |

TABLE 3

| PT RS | | Date of Assessment | | | | |
|---|---|---|---|---|---|---|
| Test | Dimension | initial | Day 7 | Day 14 | Day 21 | Day 28 |
| ABC | TOTAL | 53 | 28 | 20 | 20 | 20 |
|  | irritability | 3 | 3 | 1 | 1 | 1 |
|  | lethargy | 6 | 3 | 1 | 1 | 1 |
|  | stereotypy | 16 | 11 | 9 | 9 | 9 |
|  | hyperactivity | 20 | 8 | 6 | 6 | 6 |
|  | speech | 8 | 3 | 3 | 3 | 3 |
| DSM V | TOTAL | 21 | 15 | 8 | 6.5 | 5.5 |
|  | social | 5 | 3 | 1.5 | 1 | 1 |
|  | communication | 5 | 4 | 1.5 | 1.5 | 1.5 |
|  | relationships | 1 | 0 | 0 | 0 | 0 |
|  | behavior | 10 | 8 | 5 | 4 | 3 |

TABLE 4

| PT WC | | Date of Assessment | | | | |
|---|---|---|---|---|---|---|
| Test | Dimension | initial | Day 7 | Day 14 | Day 21 | Day 28 |
| ABC-C | TOTAL | 70 | 30 | 18 | 17 | 17 |
|  | irritability | 16 | 4 | 2 | 2 | 2 |
|  | lethargy | 21 | 9 | 3 | 2 | 2 |
|  | stereotypy | 12 | 7 | 6 | 6 | 6 |
|  | hyperactivity | 20 | 10 | 7 | 7 | 7 |
|  | speech | 1 | 0 | 0 | 0 | 0 |
| DSM-V | TOTAL | 26 | 17 | 14 | 12 | 11 |
|  | social | 6 | 6 | 4 | 2 | 2 |
|  | communication | 3 | 0 | 0 | 0 | 0 |
|  | relationships | 6 | 2 | 2 | 2 | 2 |
|  | behavior | 11 | 9 | 8 | 8 | 7 |

What is claimed:

1. A method of treating autism comprising administering to a subject in need thereof an effective amount of α-methyl-DL-tyrosine and an effective amount of γ-aminobutyric acid (GABA).

2. The method of claim 1 wherein the α-methyl-DL-tyrosine and GABA are administered simultaneously.

3. The method of claim 1, wherein the α-methyl-DL-tyrosine and GABA are administered separately.

4. The method of claim 1 wherein the α-methyl-DL-tyrosine is administered orally.

5. The method of claim 1 wherein 150-300 mg of the α-methyl-DL-tyrosine is administered daily.

6. The method of claim 5 wherein the α-methyl-DL-tyrosine is administered in three substantially equal doses.

7. The method of claim 1, wherein about 5 to about 30 mg of the GABA is administered daily.

8. The method of claim 1, wherein about 15 mg of the GABA is administered daily.

9. The method of claim 1, further comprising administering an effective amount of a p450 3A4 promoter.

10. The method of claim 9, wherein the p450 3A4 promoter is 5,5-diphenylhydantoin, valproic acid, or carbamazepine.

11. The method of claim 1 that reduces at least one of the following autism symptoms:
- deficits in social-emotional reciprocity;
- deficits in nonverbal communicative behaviors used for social interaction;
- deficits in developing, maintaining, and understanding relationships stereotyped or repetitive motor movements, use of objects, or speech;
- insistence on sameness, inflexible adherence to routines, or ritualized patterns of verbal or nonverbal behavior;
- highly restricted, fixated interests that are abnormal in intensity or focus; and
- hyper- or hyporeactivity to sensory input or unusual interest in sensory aspects of the environment.

12. The method of claim 1, wherein the method results in a reduction in at least one dimension of the Conners Parent Rating Scale assessment score.

13. The method of claim 12, wherein the method results in a reduction of at least 1 point in at least one dimension of the Conners Parent Rating Scale assessment score.

14. The method of claim 1, wherein the method results in a reduction in an irritability, lethargy, stereotypy, hyperactivity, and/or speech Aberrant Behavior Checklist-Community (ABC-C) assessment score.

15. The method of claim 14, wherein the method results in a reduction of at least 1 point in the irritability, lethargy, stereotypy, hyperactivity, and/or speech ABC-C score.

16. A method of treating tics or a symptom of Attention Deficit Disorder in a subject who has been diagnosed with autism, autism spectrum disorder, Asperger Syndrome, or Social Communication Disorder, comprising administering to the subject an effective amount of α-methyl-DL-tyrosine and an effective amount of a beta adrenergic agonist that is albuterol, levalbuterol, fenoterol, formoterol, isoproterenol, metaproterenol, salmeterol, terbutaline, clenbuterol, isoetarine, pirbuterol, procaterol, ritodrine, epinephrine, or a combination thereof.

17. The method of claim 16, wherein the beta adrenergic agonist is albuterol, levalbuterol, or a combination thereof.

18. The method of claim 16, wherein the beta adrenergic agonist is albuterol.

19. The method of claim 16 wherein the α-methyl-DL-tyrosine and the beta adrenergic agonist are administered simultaneously.

20. The method of claim 16, wherein the α-methyl-DL-tyrosine and the beta adrenergic agonist are administered separately.

21. The method of claim 16, wherein the α-methyl-DL-tyrosine is administered orally.

22. The method of claim 16, wherein 150-300 mg of the α-methyl-DL-tyrosine is administered daily.

23. The method of claim 22, wherein the α-methyl-DL-tyrosine is administered in three substantially equal doses.

24. The method of claim 16, wherein the tics are motor tics.

25. The method of claim 16, for the treatment of a symptom of Attention Deficit Disorder.

26. The method of claim 16, wherein the subject has been diagnosed with autism spectrum disorder.

27. The method of claim 16, wherein the subject has been diagnosed with Asperger Syndrome.

28. The method of claim 16, wherein the subject has been diagnosed with Social Communication Disorder.

* * * * *